United States Patent
Fanelli et al.

(10) Patent No.: US 9,182,379 B2
(45) Date of Patent: Nov. 10, 2015

(54) METHOD OF CARRYING OUT A VIBRATORY FATIGUE TEST OF A MECHANICAL PART

(71) Applicant: SNECMA, Paris (FR)

(72) Inventors: Jeremy Fanelli, Dravell (FR); Alain Bassot, Bois le Roi (FR); Michéle Marois, Hericy (FR)

(73) Assignee: SNECMA, Paris (FR)

( * ) Notice: Subject to any disclaimer, the term of this patent is extended or adjusted under 35 U.S.C. 154(b) by 296 days.

(21) Appl. No.: 13/942,304

(22) Filed: Jul. 15, 2013

(65) Prior Publication Data
US 2014/0130598 A1 May 15, 2014

(30) Foreign Application Priority Data
Jul. 16, 2012 (FR) .................................... 12 56864

(51) Int. Cl.
*G01N 29/12* (2006.01)
*G01N 3/32* (2006.01)
(Continued)

(52) U.S. Cl.
CPC ................ *G01N 29/12* (2013.01); *B23K 31/02* (2013.01); *B23K 31/125* (2013.01); *G01M 5/0016* (2013.01); *G01M 5/0033* (2013.01); *G01M 5/0066* (2013.01); *G01M 7/00* (2013.01); *G01N 3/32* (2013.01); *G06F 17/5018* (2013.01); *B23K 2201/001* (2013.01); *F05D 2260/83* (2013.01); *G01N 2203/0073* (2013.01);
(Continued)

(58) Field of Classification Search
CPC ................ B23K 2201/001; G01N 2203/0073; G01N 2203/0216; G01N 2203/0296; G01N 2203/0298

USPC ............................................ 73/577, 593, 660
See application file for complete search history.

(56) References Cited

U.S. PATENT DOCUMENTS 4,448,059 A * 5/1984 Kondo et al. ................ 73/35.09
5,620,307 A * 4/1997 Mannava et al. .......... 416/241 R
(Continued)

FOREIGN PATENT DOCUMENTS

| EP | 1 747 840 | 1/2007 |
|---|---|---|
| EP | 1 889 682 | 2/2008 |
| EP | 2 241 872 | 10/2010 |
| WO | 2012078239 | * 6/2012 |

OTHER PUBLICATIONS

Search Report and Written Opinion as issued for French Patent Application No. 1 256 864, dated Apr. 26, 2013.

*Primary Examiner* — J M Saint Surin
(74) *Attorney, Agent, or Firm* — Pillsbury Winthrop Shaw Pittman LLP (57) ABSTRACT

A method of carrying out a vibratory fatigue test of a mechanical part having a fatigue endurance limit, the part including a repair extending partly on a first zone of the part, the method including a preliminary test phase including: selecting a loading mode of the part; determining a cutting of the part defining a truncated part, the cutting of the part being defined to obtain a loading level in the repaired zone equal to the maximum value of an abatement to be validated; selecting a measuring device for the fine control of the fatigue test by the measurement of a stress applied to a point of the part; determining a resonance frequency of the truncated part according to the selected loading mode; implementing a loading according to the selected mode at a given level of the truncated part at the resonance frequency up to rupture of the part.

10 Claims, 4 Drawing Sheets

(51) Int. Cl.
*B23K 31/12* (2006.01)
*G01M 5/00* (2006.01)
*G01M 7/00* (2006.01)
*B23K 31/02* (2006.01)
*G06F 17/50* (2006.01)

(52) U.S. Cl.
CPC .......... *G01N 2203/0216* (2013.01); *G01N 2203/0296* (2013.01); *G01N 2203/0298* (2013.01); *G06F 2217/76* (2013.01)

(56) References Cited

U.S. PATENT DOCUMENTS

| | | | |
|---|---|---|---|
| 5,846,057 A * | 12/1998 | Ferrigno et al. | 416/241 R |
| 8,985,068 B2 * | 3/2015 | Nicgorski | 123/41.49 |
| 2006/0056960 A1 * | 3/2006 | Sabol et al. | 415/118 |
| 2010/0170878 A1 | 7/2010 | Krause | |
| 2013/0191040 A1 * | 7/2013 | Yoon et al. | 702/36 |
| 2013/0325373 A1 * | 12/2013 | Qiao et al. | 702/58 |

* cited by examiner

METHOD OF CARRYING OUT A VIBRATORY FATIGUE TEST OF A MECHANICAL PART

CROSS-REFERENCE TO RELATED APPLICATIONS

This application claims priority to French Patent Application No. 1256864 filed Jul. 16, 2012. The content of this application is incorporated herein by reference in its entirety.

FIELD

The present invention relates to the technical field of fatigue tests carried out on repaired parts, such as turbojet engine blades.

More particularly, the field of the invention relates to fatigue test methods after a machining of a part and a repair of said part such as a welding. Moreover, the field of the invention particularly relates to parts, which are welded to a repair part designated by "patch", which are of large dimensions. It may be a piece of sheet metal suited to substituting for the machined leading edge of the part.

BACKGROUND

Generally, in the aeronautics field, after repair of a part with a view to reuse, a certain number of tests are necessary in order to mechanically validate the part to guarantee a satisfactory lifetime after repair.

A test generally carried out is that of the vibratory fatigue test, better known under the acronym HCF designating: "High Cycle Fatigue". These tests make it possible to standardise a repair in the sense where it may then be industrialised on a large number of structurally identical parts by the same repair method while guaranteeing a satisfactory lifetime of the repaired parts.

It is thus necessary to characterise or validate the abatement of the material in HCF after repair. A known method is that called the "staircase" method, which may for example be carried out on repaired turbine blades.

However, the method comprises several drawbacks.

Figure 1:
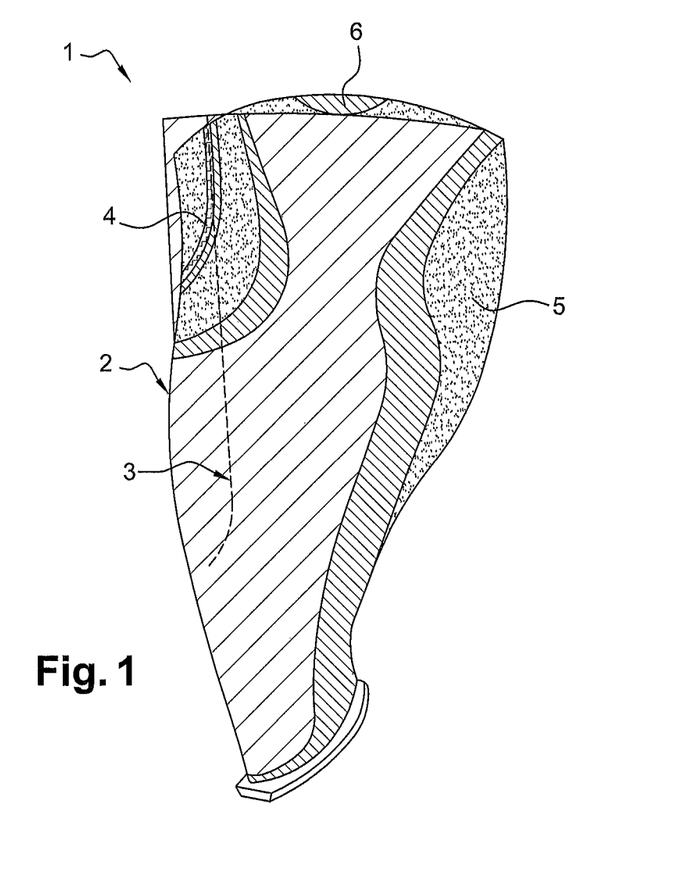
FIG. 1 represents a FAN blade comprising a damaged leading edge 25.

In the first place, the method requires loading the repaired blade according to a particular mode in order to be able to render the repaired zone critical, FIG. 1 illustrates a blade 1 having a damaged leading edge 2. The leading edge is intended to be repaired by a repair part, also called "patch" more commonly in the professional terminology. The patch is generally welded onto a surface of the part corresponding to the damaged portion. In the case of a blade, it is most often the leading edge. The repair forms at its limit a weld line 3. The test method enables stresses to be generated on the blade so as to fatigue test the repaired blade. The zones 4, 5 and 6 represent zones that deform under the effect of bendings applied to the part under vibration generating high levels of stresses. The vibratory fatigue tests are carried out at a mechanical resonance frequency of the part.

The zone 4 represents strips forming arcs of circles of which the strips the closest to the leading edge are the most deformed.

A first drawback is that this mode requires a high excitation energy to generate a sufficient level of stress in the repaired zone, which can with difficulty be generated by test means such as a vibrating table used conventionally.

The existing test method, which consists in determining the endurance limit in the weld, in other words at the level of the repair, and thus the determination of the abatement, does not make it possible to validate a maximum abatement level because the loading levels in the repaired zone are limited by the test means.

Moreover, a second drawback is the duration of a test, in other words the duration during which the part has to be vibrated at the resonance frequency of the mode in question, which is relatively long. As an example, for the first bending mode (1F) at 58 Hz, this duration is around 48 hours. Yet a particularity of the "staircase" method is that it comprises a large number of vibratory cycles for each part, by way of example at least 10,000,000 vibratory cycles for each part in current usage.

During the validation of a repair of blades by welding of a long patch on a leading edge, the cost and the duration of the test can become potentially problematic to validate the repair.

SUMMARY

An aspect of the invention enables the aforementioned drawbacks to be resolved.

An embodiment of the invention relates to a method of carrying out a vibratory fatigue test of a mechanical part having a fatigue endurance limit, the part comprising a repair extending partly on a first zone of the part.

The method includes a preliminary test phase including:
a selection of a loading mode of the part;
a determination of a cutting of the part defining a truncated part, the cutting of the part being defined so as to obtain a loading level in the repaired zone equal to the maximum value of an abatement to be validated.

The method further comprises:
a selection of a measuring device for the fine control of the fatigue test by the measurement of a stress applied to at least one point of the part;
a determination of a resonance frequency of the truncated part according to the selected loading mode;
the implementation of a loading according to the selected mode at a given level of the truncated part at the resonance frequency up to rupture of the part.

A benefit of the method is that the cutting of the part makes it possible:
on the one hand to adjust the loading level in the repaired zone so as to validate a maximum abatement value;
to reduce the resonance frequency of the part during the vibratory fatigue test, the stiffness of the part being increased. Consequently, the method of an embodiment of the invention thus makes it possible in this way to reduce the duration of the test to arrive at rupture.

Beneficially, the cutting of the part is determined by a first calculation of a sensitivity of the truncated repaired part, the sensitivity being substantially equal to the maximum abatement value.

A benefit is that the sensitivity may be calculated by a mathematical method, for example the finite element method. This calculation makes it possible to make the desired abatement correspond with the sensitivity of the repaired part.

Beneficially, the first calculation is performed by the finite element method.

Beneficially, the maximum abatement value is comprised between 40 and 50% of the endurance limit of the part.

Beneficially, the part is a turbojet engine blade, the first zone is the leading edge of the blade, the repair comprises a repair part welded onto the first zone. The repair part may be a metal sheet.

A benefit is to be able to use the method of an embodiment of the invention for large metal parts such as blades undergoing degradations, for example, on the leading edges thereof.

The latter require, after machining of the leading edge, a repair by welding of a patch forming a profiled sheet.

Beneficially, the determination of the cutting of the part comprises the determination of a cutting height and a cutting shape. A benefit is to make a simple cutting, for example horizontal. But the cutting may be of different nature, of different shape. It may be continuous or discontinuous when several cuttings are made. The finite element method applied to the repaired part makes it possible to define a cutting that enables the loading value to be adjusted (either reduced or increased) in the repaired zone while at the same time validating a maximum materials abatement.

The cutting may be transversal in a plane perpendicular to the axis of the repair part.

Beneficially, the loading mode is a bending mode applied to the part. In other embodiments, the loading mode may be different, such as a torsion. A benefit of an embodiment of the invention is that the method makes it possible to be applied to any type of test carried out on any type of repaired part. The interest of the method resides in the capacity to guarantee a sensitivity close to the desired abatement. This method can be applied to all loadings able to define a fatigue test. A benefit of the bending mode is that it represents a real stress applied to the part in an operational mode. Furthermore, it enables repairs made in a two-dimensional space to be simply fatigue testes, the bending being perpendicular to the repaired surface.

According to an embodiment, the resonance frequency may either be estimated by a mathematical method of modelling the truncated part for example by the finite element method, or be determined by a search by testing different vibration frequencies until that which enables the part to be made to resonate is found.

The two modes may be combined so as to perform a first estimation and then to search locally for the most suitable.

A benefit of the choice of this bending mode, also called 1 F mode, is that it constitutes a first dimensioning test, representative of the quality of the desired repair.

Beneficially, a step of measuring the sensitivity during the test is carried out by means of a set of sensors arranged on the truncated repaired part enabling:
  a first reading of the stress in the first zone and;
  a second reading of the stress in a zone of the part,
  the ratio between the first reading and the second reading being compared to a ratio calculated at the same points of the truncated repaired part by the finite element method.

This method makes it possible to measure the sensitivity of the weld accurately and to correlate it with the calculation obtained by a mathematical method of approximation. This step enables the hypotheses taken to be validated, particularly the realisation of a mathematical model.

Beneficially, a step of determining a loading intensity of the part is carried out so as to obtain a rupture of the part after a predetermined duration. This makes it possible to be compliant with fatigue test norms exerted on a determined number of cycles.

Beneficially, the measurement device comprises:
  at least one first sensor in the first zone of the truncated repaired part;
  at least one second sensor in a second zone of the truncated repaired part in which the fatigue stress value is substantially close to the maximum value.
  at least one third sensor enabling the fine control of the test, the third sensor being situated in a third zone where the gradient of the stresses is minimal during the loading of the part.

The fine control of the test makes it possible in particular to adjust the vibration frequency to find simply the resonance frequency approximated by the calculation. The fine control also makes it possible to verify the levels of stresses applied to certain zones and to compare them with a mathematical model, for example that of the finite element model.

BRIEF DESCRIPTION OF DRAWINGS

Other characteristics and benefits of embodiments of the invention will become clearer on reading the detailed description that follows, with reference to the appended figures, which illustrate.

DETAILED DESCRIPTION

In the remainder of the description, a loading mode of a part designates a loading applied to the part with a view to obtaining deformation of the part. The loading of the part carried out in a repeated manner on the part enables a fatigue test to be defined.

A loading may be for example a bending or a torsion of the part. It is generally expressed in a referential of the part.

In the remainder of the description, a "bending mode" designates a bending applied to a mechanical part in a given direction. A bending mode may be characterised by the number of inflection points of the deflection curve of a part under stresses generated by bending loads. A mode called "1F" generates one inflection point of the deflection curve of the tested part under stresses. The "2F" mode generates two inflection points of the deflection curve of the tested part under stress. The notation applies to the modes NF generating N (whole N) inflection points of the deflection curve of the part.

Each vibratory bending mode includes a resonance frequency for the tested part.

The bending load on the part is defined along a direction transversal to the greatest length of the part to be fatigue tested.

"Patch" designates a repair part intended to be superimposed on a damaged zone of a mechanical part. The patch is generally welded onto the damaged zone. In an example, a patch is a metal sheet welded onto a leading edge of a turbojet engine blade.

"Frequency scan" designates the manipulation consisting in searching for a frequency in a frequency range having the desired properties. Typically, to search for a vibration frequency of a mechanical part, a frequency scan is the operation aiming to try several frequencies so as to find that which makes the part enter into vibration. A frequency scan method may be carried out by dichotomy.

In the remainder of the description, a "fatigue endurance limit" of a metal part designates the value of the maximum load applied in fatigue for which, according to a given test configuration, the part maintains an infinite lifetime.

In the remainder of the description, an "abatement" designates a proportion expressed in percentage corresponding to a level of reduction of the fatigue endurance limit of a mechanical part.

An abatement of 40% corresponds to a 40% reduction of the maximum limit value of the fatigue stress applicable to a part so that it maintains an infinite lifetime.

In the remainder of the description, the "sensitivity $S_P$" of a point P of the tested part (the tested part including all the elements linked to the part such as repairs, welds or a patch) designates the ratio between the value of the maximum stress at the point P and the value of the maximum stress of the part measured at a point of the part.

Generally, the point where the value of the stress is maximal in a part such as a compressor blade for bending stresses is the foot of the blade. Vibratory fatigue tests enable this point to be determined, it is thus in general known and can constitute a known data of the method of the invention described hereafter.

The sensitivity of a part comprising a repair is by default: the ratio between the value of the stress at a point P of the repair where the maximum stresses are exerted and the value of the maximum stress of the part measured at a point of the part.

Figure 2:
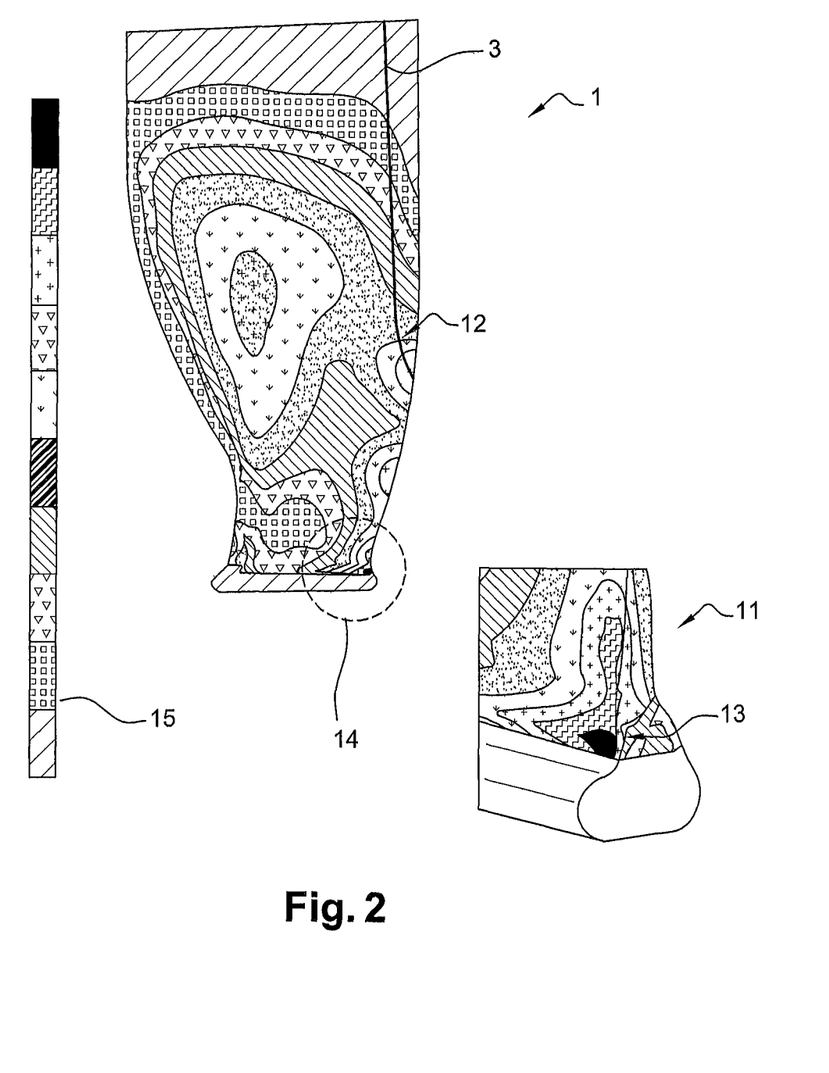
FIG. 2 represents a FAN blade subjected to a fatigue test according to the method of an embodiment of the invention.

FIG. 2 represents a blade 1 subjected to a vibratory fatigue load according to a first bending mode. The blade includes a patch welded by means of a weld 3 extending along the leading edge of the blade 1.

When the blade is subjected to the vibratory fatigue load, a distribution of the stresses may be read, particularly by means of sensors by measurements. The reading of the values during the test makes it possible for example to finely control a test particularly by comparison with the expected values and estimated by a calculation method, such as that of the finite element method.

A first zone 12 of the part may be identified as supporting the maximum stresses in the weld and a second zone 14 of the blade may be identified as supporting the maximum stresses of the part.

A zoom 11 of the blade 1 enables the blade foot to be visualised and to precisely locate the position of the point where the maximum stress is exerted in the part.

A scale 15 makes it possible to represent the diagram of the maximum and minimum stresses in all the zones of the part deformed under the effect of a bending load.

In a blade subjected to bending loads, the blade being maintained by the foot on a test means such as a vibrating table, the maximum stresses are generally localised in a zone situated at the foot of the blade.

The sensitivity of a part may be calculated by the ratio between a value of maximum stresses exerted at a point P of the repair zone of the part and the maximum value exerted on the part. This calculation may be performed by a modelling of the stresses, for example by means of the finite element method.

Moreover, the measurement may be validated during the fatigue test by the reading, by means of sensors, of stress values at points where the values may be calculated. A sensitivity relative to a sensor may be measured and compared to a calculated sensitivity. This is the case when the zone having the maximum stresses is difficult to reach by measurement means. It is possible to place the sensors at places where the stresses are not maximal, the aim being to validate the calculation model.

Two positions for the placement of sensors are determined;
a first position corresponding to the point P of maximum stress in the weld or a nearby zone if the first position is inaccessible and;
a second position corresponding to the point of maximum stress in the part or a nearby zone if the second position is inaccessible.

The reading of stresses makes it possible to validate or to correct the calculation of the ratio between the value of the maximum stress at the point P and the value of the maximum stress of the part measured at a point of the part.

In order to check that a repair of a part such as a weld is validated, it is desirable to check by a fatigue test the repaired part and to note that the destructive test causes a rupture in the part elsewhere than in the weld. Which amounts to validating the correct repair carried out on the part.

Since fatigue tests are relatively long, it is desirable to reduce the duration thereof. Given the large dimensions of the parts, for example compressor blades, the method of an embodiment of the invention makes it possible to reduce the largest dimension particularly by making a cutting of the part to reduce the length thereof.

The method of an embodiment of the invention comprises a step making it possible to calculate or to measure the sensitivity in the weld, in other words the repaired zone, after the cutting of the part.

In an embodiment, when the maximum desired abatement value is 50%, the cutting of the part to be fatigue tested is carried out so as to guarantee a sensitivity at a point P of the weld substantially equal to 50%. In other words that the cutting is carried out by maintaining the following condition: $S_P=50\%$. This condition makes it possible to validate an abatement of the part less than or equal to 50%.

According to embodiment variants, the value of the sensitivity $S_P$ at a point of maximum stress of the weld of the part may be, chosen in a range comprised between about 40% and about 50%, which enables a good compromise between: on the one hand, the desired reduction of the part and thus the time saving obtained for carrying out the test and on the other hand a control representative of the quality of repair.

The method of an embodiment of the invention includes a preparatory phase to the vibratory fatigue test. This phase includes the determination of a cutting of the part in its longest length, which is substantially perpendicular to be bending loads that are generated during the tests.

Any cutting making it possible to guarantee a desired maximum abatement may be carried out according to the method of an embodiment of the invention. When the part is a blade, the latter is cut in its upper part, in other words the part opposite the foot of the blade.

A simple cutting consisting in determining a cutting height defined from the foot of the blade is a cutting shape: for example a horizontal cutting.

The cutting and thus the cutting height may be determined so as to obtain sensitivity in a point of the part where the weld is situated substantially equal to the maximum abatement value to be validated while remaining above this threshold. An example of appropriate threshold is to choose a sensitivity substantially above 50% for example. The sensitivity may be calculated. When it is calculated, it may be approached by a mathematical method, for example the finite element method. It may be validated while the test is being carried out as explained previously by a reading of measurements at certain points, which will be compared with the measured values.

The method, enabling a truncated part to be tested in its length, or its height, also makes it possible at the same time to adjust the sensitivity at a point of the weld while guaranteeing a sensitivity greater than 50%. Hence, the method makes it possible to adjust the part to the "strictly necessary" of the repair that it is wished to validate. The choice of an adjusted cutting height makes it possible to approach a desired sensitivity at any point of the weld while obtaining an abatement value necessary to validate the repair.

The part thereby cut moreover makes it possible to reduce the duration of the vibratory fatigue test.

Figure 3:
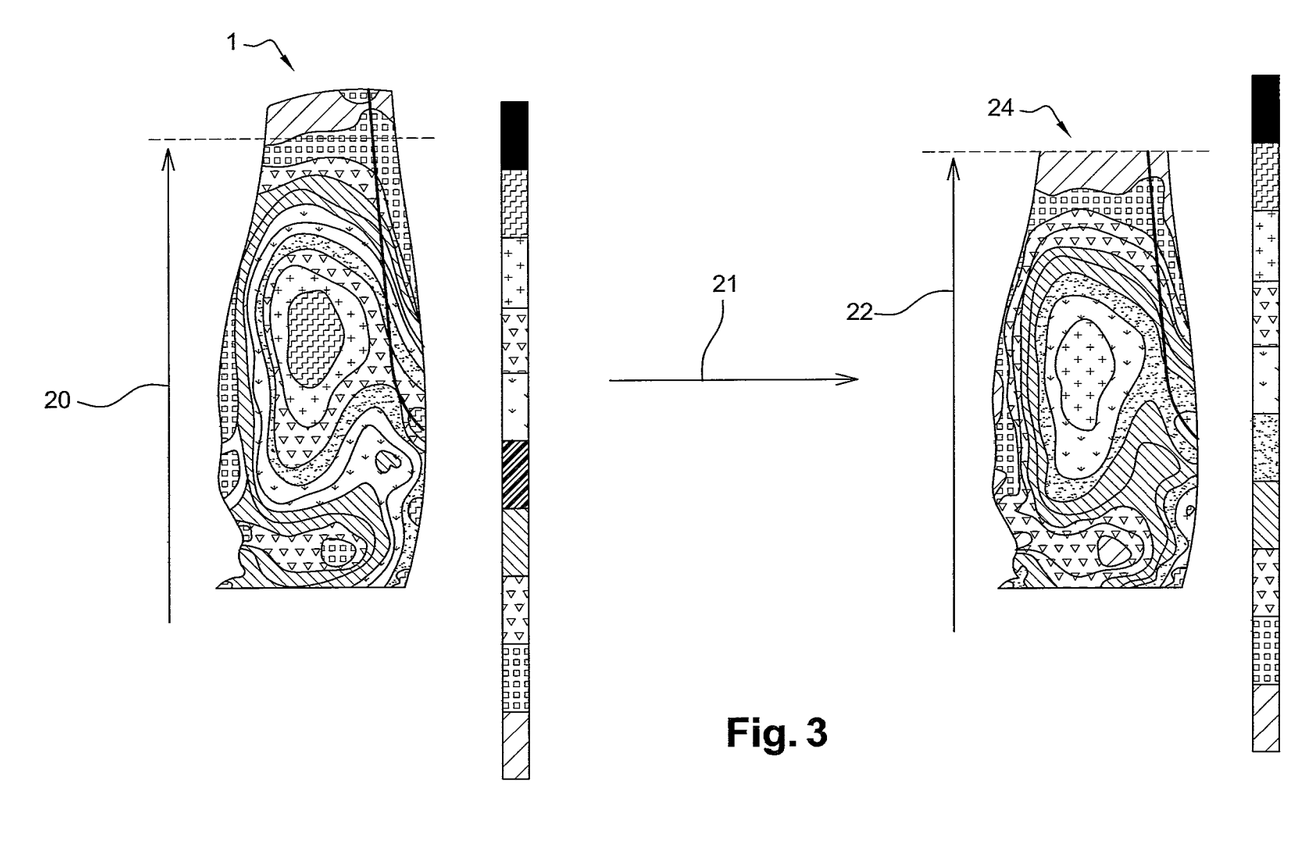
FIG. 3 represents a cutting of a FAN blade according to the method of an embodiment of the invention.

FIG. 3 represents a blade having an initial height 20 and a height 22 after the step of cutting 21. The shape of the cutting 24 may be simply horizontal, in other words in a plane perpendicular to the longest dimension of the blade.

FIG. 3 also represents the distribution of standardised dynamic stresses on a 1F bending mode for a FAN blade truncated at 500 mm height. The distribution of the stresses is modified accordingly by the cutting but the zones of maximum stresses remain localised at the same places. The test aiming to control the fatigue strength of a repaired part is validated by the search for a sensitivity at a point of the weld above a certain threshold, for example 50%.

The method of an embodiment of the invention includes in this preparatory phase a step of instrumentation that comprises the choice of sensors and the implementation thereof on the part. The sensors may be gauges, making it possible to measure the surface stresses that are exerted on the deformed part.

Figure 4:
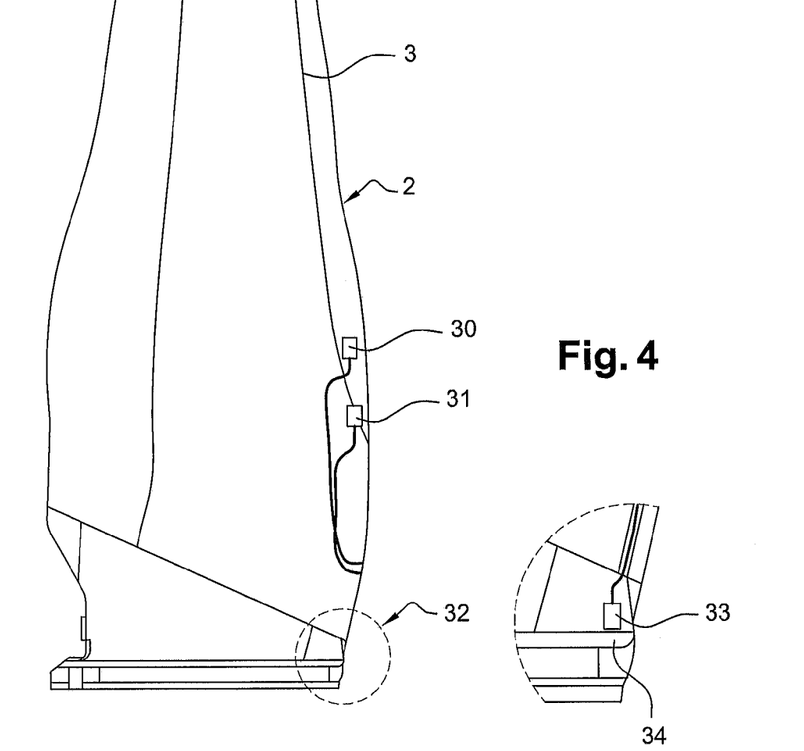
FIG. 4 represents an instrumentation of the FAN blade according to the method of an embodiment of the invention.

A possible configuration is to arrange three gauges in different zones, as represented in FIG. 4.

A gauge 30 is arranged in a zone of the part or a zone of the patch that has an average variability of stresses. This gauge 30 makes it possible to finely control the test by the measurement of the stresses observed at this point. The stresses are readings by the gauge and interpreted by means of a computer and for example a display making it possible to monitor the evolution of stresses and to carry out calculations of average stresses and maximum stresses. The gauge 30 makes it possible in particular to calibrate the level of bending loads to generate to arrive at a resonance of the part under test.

A gauge 31 is arranged at the point of the part undergoing the maximum stress of the welded zone. It is situated on the surface of the patch covering the part and welded thereto. It makes it possible to measure the maximum stress in the weld. One speaks of a gauge in the weld. In a more general case, which applies to other repairs, a gauge 31 is arranged in the repair zone undergoing the greatest stresses.

A gauge 33 is arranged in a zone of the part undergoing the maximum stresses vis-à-vis the stresses undergone over its whole surface. The zone 32 including a point where the gauge 33 is arranged is shown in zoom. It is situated at the foot of the blade when the latter constitutes the mechanical part to be tested in a zone situated in the blend radius between the stilt and the span of the blade. This gauge 33 makes it possible to measure the maximum stress undergone by the mechanical part.

In practice, the gauge 33 may be situated in a zone in the vicinity of the point 34 of the part where the stresses are maximal in so far as an approximation may suffice to calculate the sensitivity of the part in the weld. An approximation of the order of 15% of the levels of maximum stresses measured vis-à-vis the actual maximum level remains acceptable and leaves a certain flexibility for the realisation of the instrumentation of the test. In fact, such an approximation enables a margin of error on the positioning of the gauges vis-à-vis the positions of actual maximum stresses.

When the zones where the maximum stresses are exerted are difficult to reach by sensors, another possibility is to read the measurements at "control" points as close as possible to the maximum values of stresses and to compare these measurements to those calculated so as make corrections to the model.

The method of an embodiment of the invention in its preparatory phase thus comprises the cutting itself of the part. Any device or apparatus for cutting a blade may be used. Since the test is destructive, no finishing requirement of the cutting is restrictive of an embodiment of the invention. The cutting may be carried out in a plane perpendicular to the biggest direction of the part to be tested. On the other hand, it is desirable to conserve a sensitivity greater than the predetermined threshold, for example 50%. The cutting height may be calculated so as to guarantee this requirement.

The method of an embodiment of the invention comprises a phase of vibratory fatigue testing of the mechanical part to be tested.

This phase comprises a step of positioning the part on a device or apparatus (e.g. a vibrator) enabling vibrations to be generated in a regular manner. A vibrating table conventionally used to carry out vibratory fatigue tests is suitable for carrying out the test method. The part is maintained at the level of the foot thereof and extends in the greater dimension therefore in height on the table.

The test comprises a step of frequency scan so as to identify by measurement the new vibration frequency of the cut part. It involves searching for the resonance frequency of the repaired part. The truncated part being shorter than the part before the cutting, a benefit of an embodiment of the invention is to naturally raise the resonance frequency of the part. In fact, when the part is a blade, the maximum deflection at the end of the truncated blade under the effect of a bending load is smaller than that of a non-truncated blade. Consequently, the resonance frequency of the part in a vibratory fatigue mode is naturally increased by the effect of cutting the part.

The resonance frequency may be estimated by a calculation method and then approached during the test by the method of a frequency scan. The two methods may be complementary and be combined to save time during the test.

The resonance frequency being raised, the duration of the vibratory fatigue test is reduced for an equivalent quality of validation of the repair of the part, particularly a weld in the case of a welded blade.

The method of an embodiment of the invention thus enables a time saving in the length of the vibratory fatigue test.

The method of an embodiment of the invention in its phase of carrying out the vibratory fatigue test comprises, moreover, a measurement of the distribution of the stresses of the whole of the blade when it is subjected to a bending load for example in 1F mode. Which makes it possible to ensure that the sensitivity measured in the weld indeed corresponds to the values calculated beforehand for example by a mathematical method such as the finite element method.

The first read values of the test thus make it possible to validate that the sensitivity of the weld is at least equal to 50% when the value corresponds to the admissible threshold for validating the test.

The measured values can be measured by means of sensors such as the previously evoked gauges.

Finally, the method of an embodiment of the invention in its phase of carrying out the vibratory fatigue test comprises a step of placing in vibratory fatigue the part at resonance frequency up to rupture of the part.

Noting the place of rupture or fissure of the part after the test has ended makes it possible to validate the repair and the implementation of the repair for a certain number of parts.

The loading level of the part is adjusted as a function of the number of cycles to rupture obtained for a previous test carried out on another blade.

Figure 5:
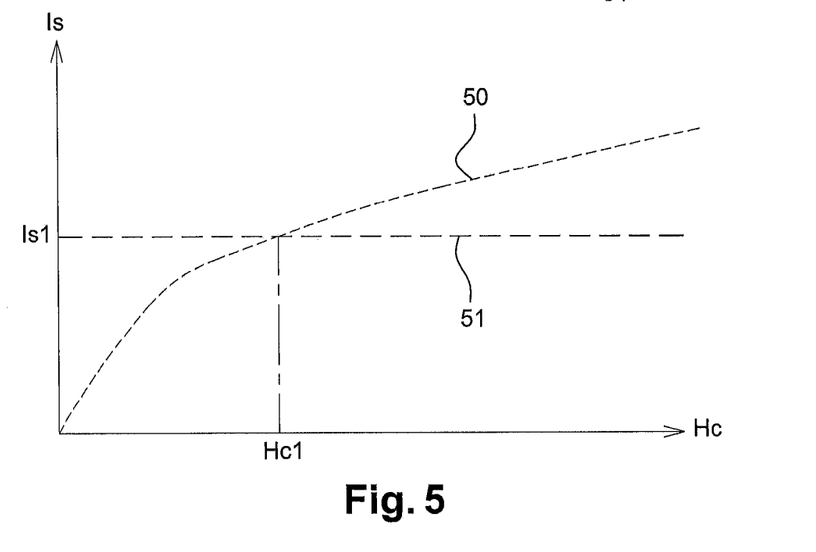
FIG. 5 represents curves defining the minimum cutting height to make on a repaired part to guarantee a given loading level in the repaired zone to validate a materials abatement value in the zone.

FIG. 5 represents a mark making it possible to establish a function between a cutting height Hc of a part and the loading level Is to apply in the repaired zone of the repaired part.

A first curve 51 represents a target loading level $I_{S1}$ to apply to the repaired zone of the repaired part to validate a maximum materials abatement value in the repaired zone.

The curve 50 is obtained by the finite element method applied to a repaired part. It represents the loading level in the repaired zone to apply according to the cutting height Hc.

The part may thus be cut to the minimum height Hc1 to guarantee at least the target loading level in the repair zone of the repaired part.

The cutting has the effect of increasing the stiffness of the part and thus the resonance frequency thereof. As an example, the frequency corresponding to the 1F mode of the non-truncated FAN blade is around 58 Hz (i.e. 4.8 h to attain 1,000,000 cycles). With the cutting presented previously (500 mm), the frequency rises to 75 Hz (i.e. 3.7 h to attain 1,000,000 cycles). At equal number of cycles, around 1 hour of test per part is gained, i.e. around 1 test day for 6 parts. This increase in the resonance frequency contributes to a reduction in the necessary test duration.

The test method of an embodiment of the invention makes it possible to adapt a fatigue test of a part while maintaining an already operational conventional bench. It includes a great adaptability to traditional vibratory fatigue test benches for example comprising a vibrating table.

The method also includes a great flexibility vis-à-vis the configuration of the part to be tested since the latter may be cut and adjusted so as to determine a cutting height and shape enabling an abatement to be validated.

The principal benefit of an embodiment the invention is to propose a time saving and thus a cost saving of a vibratory fatigue test.

The method also makes it possible to reduce the number of parts needed to carry out vibratory fatigue tests.

The fact of truncating the part makes it possible to attain more rapidly the number of cycles to rupture and thus to reduce the test time. Moreover, this makes it possible to validate the "strictly necessary", in other words the maximum abatement value.

This methodology of validation of a material abatement in vibratory fatigue may be applied to all turbine jet blades, as well as to other types of repairs or discrepancies compared to the definition for which it is sought to validate a vibratory fatigue abatement.

In fact, the repair may be a weld for maintaining a patch on the leading edge of a blade. But the invention relates to any other link making it possible to maintain a patch on the surface of the leading edge of a part.

The method of an embodiment of the invention to be adapted may comprise:
- an estimation of the maximum abatement at N % to validate, these values are dependent on the materials used;
- a determination of the vibratory mode to excite by a test to demonstrate that one has an abatement below N %;
- a definition of the height and of the shape of the cutting of the blading in order to obtain a sensitivity Sp close to N % at the point of the repair where the stresses are maximal.

The considered sensitivity Sp of the maximum stress at a point of the repair should preferably be at least 5% above the value calculated by a mathematical method. This margin makes it possible to overestimate the actual sensitivity that will be obtained by the measurements during the test.

What is claimed is:

1. A method of carrying out a vibratory fatigue test of a mechanical part having a fatigue endurance limit, said part comprising a repair extending partly on a first zone of said part,
said method comprising a preliminary test phase including:
selecting a loading mode of the part;
determining a cutting of the part defining a truncated part, the cutting of the part being defined so as to obtain a level of loading in the repaired zone equal to a maximum value of an abatement to be validated;
said method further including:
selecting a measuring device for the fine control of the fatigue test by the measurement of a stress applied to at least one point of the part;
determining a resonance frequency of the truncated part according to the selected loading mode;
implementing a loading according to the selected mode at a given level of the truncated part at the resonance frequency up to rupture of said part.

2. The method of carrying out a vibratory fatigue test according to claim 1, wherein the cutting of the part is determined by a first calculation of a sensitivity of the truncated part, said sensitivity being substantially equal to the maximum value of the abatement.

3. The method of carrying out a vibratory fatigue test according to claim 2, wherein the sensitivity value is comprised between 40 and 50% of the endurance limit of the part.

4. The method of carrying out a vibratory fatigue test of a part according to claim 2, wherein the sensitivity during the test is determined by a set of sensors arranged on the truncated part enabling;
a first reading of at least one stress value in the first zone and;
a second reading of at least one stress value in a second zone of the part,
the ratio between the first reading and the second reading being compared to a ratio calculated at the same points of the truncated part by the finite element method.

5. The method of carrying out a vibratory fatigue test according to claim 1, wherein
the part is a turbojet engine blade;
the first zone is the leading edge of the blade;
the repair comprises a repair part welded onto the first zone.

6. The method of carrying out a vibratory fatigue test according to claim 1, wherein determining the cutting of the part comprises determining a cutting height and a cutting shape.

7. The method of carrying out a vibratory fatigue test of a part according to claim 6, wherein the shape of the cutting is transversal in a plane perpendicular to the axis of the repair part, 8. The method of carrying out a vibratory fatigue test of a part according to claim 6, wherein the loading mode is a bending mode applied to the part.

9. The method of carrying out a vibratory fatigue test of a part according to claim 1, wherein the measurement device includes:
a first sensor in the first zone of the truncated part;
a second sensor in a second zone of the truncated part in which the fatigue stress value is substantially close to the maximum value.

a third sensor enabling the fine control of the test, said third sensor being arranged in a third zone where a gradient of the stresses is minimal during the loading of the part.

10. A method of carrying out a vibratory fatigue test of a mechanical part having a fatigue endurance limit, said part comprising a repair extending partly on a first zone of said part, said method comprising:

selecting a loading mode of the part;

determining a cutting of the part defining a truncated part, the cutting of the part being defined so as to obtain a level of loading in the repaired zone equal to a maximum value of an abatement to be validated;

determining a resonance frequency of the truncated part according to the selected loading mode;

loading the part according to the selected mode at a given level of the truncated part at the resonance frequency up to rupture of said part, and measuring a stress applied to at least one point of the part.

* * * * *